(12) United States Patent
Pole et al.

(10) Patent No.: US 10,779,990 B2
(45) Date of Patent: Sep. 22, 2020

(54) OPHTHALMIC INCISIONAL PROCEDURE INSTRUMENT AND METHOD

(71) Applicant: EyeMDengineering LLC, Leawood, KS (US)

(72) Inventors: Christopher J. Pole, Leawood, KS (US); Krishi Peddada, Cupertino, CA (US)

(73) Assignee: EYEMDENGINEERING LLC, Leawood, KS (US)

( * ) Notice: Subject to any disclaimer, the term of this patent is extended or adjusted under 35 U.S.C. 154(b) by 226 days.

(21) Appl. No.: 15/899,784

(22) Filed: Feb. 20, 2018

(65) Prior Publication Data

US 2018/0235810 A1 Aug. 23, 2018

Related U.S. Application Data

(60) Provisional application No. 62/460,660, filed on Feb. 17, 2017.

(51) Int. Cl.
*A61F 9/01* (2006.01)
*A61F 9/013* (2006.01)
*A61B 17/30* (2006.01)

(52) U.S. Cl.
CPC .......... *A61F 9/0133* (2013.01); *A61F 9/0136* (2013.01); *A61B 2017/306* (2013.01); *A61B 2217/005* (2013.01)

(58) Field of Classification Search
CPC ......... A61B 17/32053; A61B 2017/306; A61F 9/0133; A61F 9/0136; A61F 9/013
See application file for complete search history.

(56) References Cited

U.S. PATENT DOCUMENTS

| | | | | |
|---|---|---|---|---|
| 4,619,259 A | * | 10/1986 | Graybill | A61F 9/013 606/107 |
| 4,691,716 A | * | 9/1987 | Tanne | A61B 3/1005 33/512 |
| 4,739,761 A | | 4/1988 | Grandon et al. | |

(Continued)

OTHER PUBLICATIONS

"International Search Report and Written Opinion for Application No. PCT/US2014/020848, dated Nov. 11, 2014".

*Primary Examiner* — Alexander J Orkin
(74) *Attorney, Agent, or Firm* — Law Office of Mark Brown, LLC; Ryan S. Hinderliter; Mark E. Brown

(57) ABSTRACT

An incisional instrument and method of use for creating accurate, reproducible surgical incisions. An exemplary embodiment includes an incisional instrument configured for attachment to a patient's eye and for use performing arcuate limbal relaxing incisions (LRIs). The incisional instrument is made up of two coaxial, interconnecting pieces: a docking piece and a cutting piece. The docking piece includes a suction mechanism and is configured for being secured to a patient's eye just outside the corneal limbus. The cutting piece is configured to fit flush within the docking piece and includes cutting blades and one or more handles for rotating the cutting piece relative to the docking piece. When assembled, the cutting blades extend beyond the proximal end of the docking piece by a length equal to the desired depth of LRIs to be cut. The incisional instrument further includes measurement markings for properly positioning and measuring incisions.

17 Claims, 4 Drawing Sheets

(56) References Cited

U.S. PATENT DOCUMENTS

| | | | |
|---|---|---|---|
| 4,796,623 A * | 1/1989 | Krasner | A61F 9/013 600/565 |
| 4,884,569 A | 12/1989 | Fedorov et al. | |
| 5,403,335 A * | 4/1995 | Loomas | A61F 9/013 606/161 |
| 5,938,674 A * | 8/1999 | Terry | A61F 9/013 606/161 |
| 6,019,472 A | 2/2000 | Koster et al. | |
| 6,143,010 A * | 11/2000 | Silvestrini | A61F 9/013 606/166 |
| 6,251,118 B1 * | 6/2001 | Proudfoot | A61F 2/147 606/166 |
| 6,613,061 B1 * | 9/2003 | Olson | A61F 2/148 606/166 |
| 7,166,117 B2 * | 1/2007 | Hellenkamp | A61F 9/013 606/166 |
| 8,231,643 B2 | 7/2012 | Davis | |
| 9,795,509 B2 | 10/2017 | Heitel et al. | |
| 2002/0103481 A1 | 9/2002 | Fader et al. | |
| 2006/0287663 A1 * | 12/2006 | Gayheart | A61F 9/0133 606/166 |
| 2007/0093795 A1 | 4/2007 | Melcher et al. | |
| 2008/0033463 A1 * | 2/2008 | Stoken | A61F 9/0133 606/167 |
| 2008/0281303 A1 | 11/2008 | Culbertson | |
| 2009/0137989 A1 | 5/2009 | Kataoka | |
| 2009/0182310 A1 | 7/2009 | Gertner et al. | |
| 2009/0182312 A1 | 7/2009 | Gertner et al. | |
| 2009/0287232 A1 | 11/2009 | Davis | |
| 2010/0022994 A1 | 1/2010 | Frey et al. | |
| 2011/0251630 A1 | 10/2011 | Richardson | |
| 2011/0319873 A1 | 12/2011 | Raksi et al. | |
| 2012/0283557 A1 | 11/2012 | Berlin | |
| 2013/0041354 A1 | 2/2013 | Brownell et al. | |
| 2013/0103014 A1 | 4/2013 | Gooding et al. | |
| 2018/0036168 A1 | 2/2018 | Heitel et al. | |

* cited by examiner

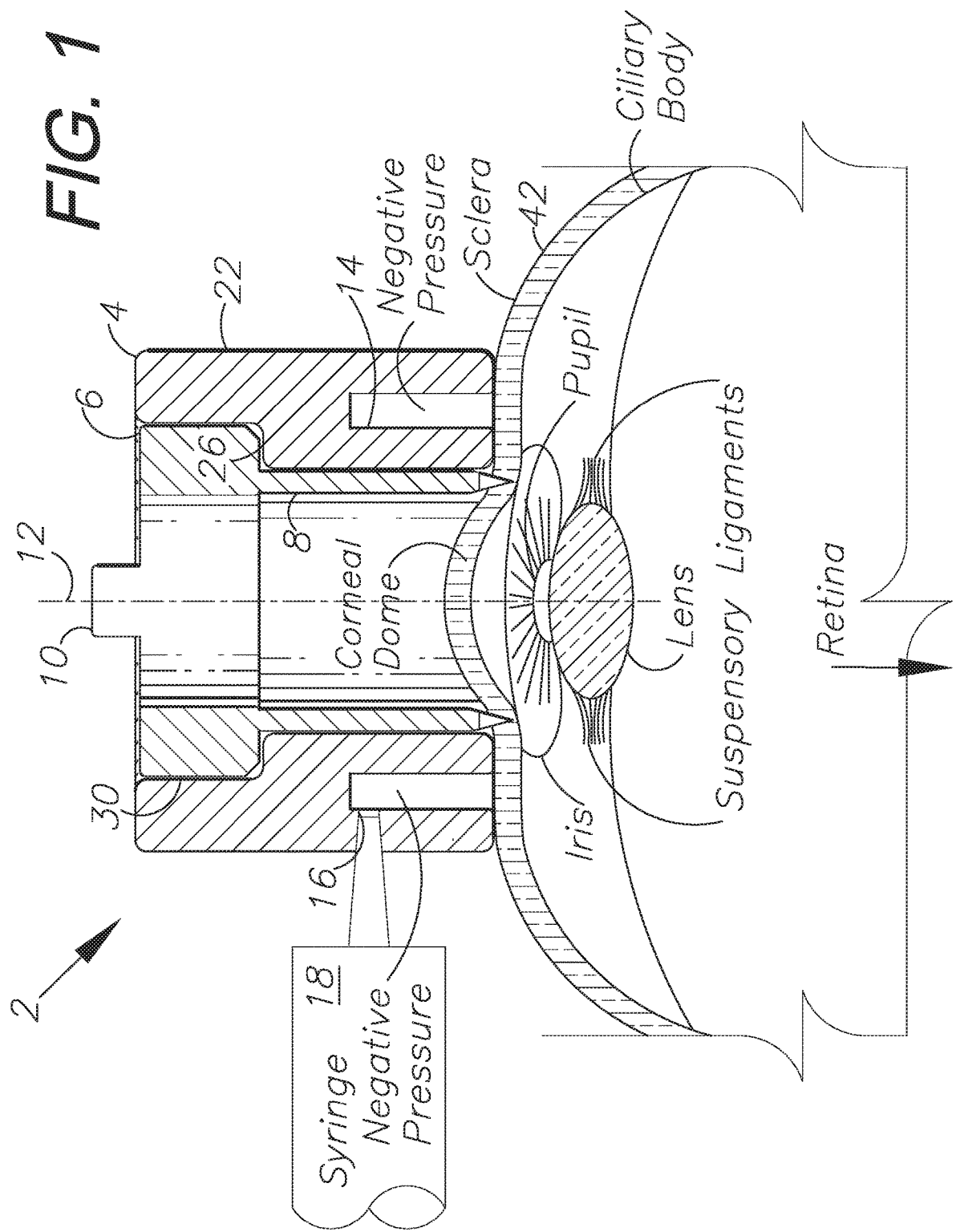

OPHTHALMIC INCISIONAL PROCEDURE INSTRUMENT AND METHOD

CROSS-REFERENCE TO RELATED APPLICATION

This application claims priority in U.S. Provisional Patent Application No. 62/460,660, filed Feb. 17, 2017, which is incorporated herein by reference.

BACKGROUND OF THE INVENTION

1. Field of the Invention

The present invention relates generally to an incisional instrument and method for performing surgical incisions, and more specifically to an ophthalmic incisional instrument for surgical correction of astigmatism and a corresponding method of performing a surgical procedure.

2. Description of the Related Art

Astigmatism is a type of visual refractive error caused by aberrant meridians of curvature around an otherwise spherical cornea or lens. These mismatched curvatures cause images to not be properly focused on the retina, resulting in blurry or distorted vision. Other symptoms of astigmatism may include eyestrain, discomfort, headaches, difficulty with night vision, and squinting. Astigmatism is very common, with studies showing approximately 15-30% of the adult population having astigmatism greater than one diopter.

Incisional methods for correction of corneal astigmatism have been popular since the 1980s. Originally, incisions to correct corneal astigmatism were made in the para-central cornea, but over the years, ophthalmologists have gradually placed these incisions further from the center of the eye because of problems with healing, predictability, and glare. Today, incisions to correct corneal astigmatism are placed in the surgical limbus, which is located at the intersection of the cornea and the sclera. These incisions are commonly referred to as limbal relaxing incisions (LRIs). Based on the degree and distribution of corneal astigmatism to be corrected, surgeons plan the arc and depth of the incisions in order to make the cornea more spherical and to improve the patient's vision.

A cataract is another very common optical condition in which the natural lens of the eye becomes cloudy, causing distorted vision. Cataract surgery—in which a patient's natural lens having a cataract is removed and replaced with an artificial intraocular lens (IOL) to restore clear vision—is currently one of the most common surgical procedures in the United States. Most people develop cataracts as they age, and thus, many patients undergo cataract surgery in each eye to correct their vision. With the prevalence of cataract treatment procedures, many ophthalmologists recommend that patients undergo surgical correction of astigmatism at the same time as cataract surgery. This option is very popular among patients because, when coupled with the spherical correction from a new intraocular lens, surgical astigmatism correction can often give these patients an opportunity to be completely free of eyeglasses and contact lenses.

Currently, there are two common methods for performing LRIs: manual incision and use of a femtosecond laser. Manual incision procedures are commonly performed with surgeons using marking pens to indicate the areas of paired incisions and then using blades, typically made of diamond or sometimes metal, to cut the LRIs. However, this method of manual incision is generally reliant on the surgeon to perform LRIs at the correct depth, length, and curvature.

A femtosecond laser accommodates automation of many factors of LRIs. This method utilizes a suction cup to hold the patient's eye in place while a laser creates the incisions from above by generating a light beam and using a scanner to deflect the light beam to deliver a treatment pattern to the surgical limbus. Femtosecond lasers are versatile, as they can be used to further automate other steps required in cataract surgery. However, the costs associated with using femtosecond lasers tend to be relatively high. Additionally, some current literature suggests that the use of such lasers does not improve outcomes in cataract surgery.

Thus, there is a strong need for a simple, inexpensive instrument and method of use thereof to assist ophthalmologists in creating accurate and reproducible manual limbal relaxing incisions (LRIs). Such an instrument could make LRIs during cataract surgery much more prevalent and provide a number of benefits for patients. Such benefits to patients include the cosmetic benefits of no longer needing to wear glasses and the benefits of no longer needing to deal with the hassle and the risks of corneal ulcers or abrasions from contact lenses. Additionally, it could ease the financial burden of having to continually purchase glasses and contact lenses. Further, such an instrument could help many patients in lower resource areas of the world, who do not have the means to obtain adequate glasses regularly, with better access to improved vision.

Currently, there are ophthalmic incisional instruments on the market consisting of a spring-loaded rod having a cutting blade in which the exposed length of the blade can be controlled with a micrometer thread. However, with such an instrument, the surgeon is still responsible for accurately guiding the instrument along the limbus and making the incision to the desired length.

Another instrument, called the Universal Limbal Relaxing Incision Guide, disclosed in U.S. Pat. No. 8,231,643, includes two concentric rings for guiding a surgeon's blade to make an incision of the appropriate measured length. This instrument helps reduce some issues with incision length and blade position of LRIs. However, the Universal Limbal Relaxing Incision Guide does not attach or anchor to the eye during the surgical procedure, making the accuracy of the LRIs reliant on the surgeon or an assistant holding the instrument in the proper position without moving. Also, there is no cutting blade portion of the Universal Limbal Relaxing Incision Guide, meaning a separate blade must be used along with it to cut the LRIs.

Heretofore there has not been available a system or method for performing LRIs with the advantages and features of the present invention.

SUMMARY OF THE INVENTION

The present invention provides an ophthalmic incisional instrument and method for creating accurate and reproducible surgical incisions. In the practice of an aspect of the present invention, the ophthalmic incisional instrument is configured for attachment to a patient's eye and for use cutting circumferential limbal relaxing incisions (LRIs) of a desired depth, length, and curvature. In a preferred embodiment, the incisional instrument is made up of two concentric, interlocking pieces: a docking piece and a cutting piece.

The docking piece includes a suction mechanism and is configured for being secured to a patient's eye just outside the corneal limbus. The cutting piece is configured to fit flush inside the docking piece and includes two cutting blades and one or more handles configured to rotate the cutting piece relative to the docking piece. When assembled, the cutting blades of the cutting piece extend beyond the bottom of the docking piece a length equal to the desired depth of LRIs to be cut. Further, the cutting piece is sized and the cutting blades are positioned such that the cutting piece is configured for making incisions along the corneal limbus when the instrument is assembled. The docking piece also includes measurement markings around its circumference, and the cutting piece includes markings configured for matching up with the docking piece markings for properly positioning and measuring incisions.

In the practice of an aspect of the present invention, a patient's eye is first marked for desired LRIs to be cut. Next, the docking piece is docked to the eye in desired position via suction. The surgeon then matches the markings on the cutting piece with the appropriate measurement markings on the docking piece to line up the cutting blades for making incisions at the desired positions. Once the markings are properly aligned, the cutting piece is inserted completely into the docking piece so that the cutting piece is flush against the docking piece, resulting in the cutting blades being inserted a predetermined, desired depth into the patient's eye. The surgeon then rotates the cutting piece relative to the docking piece a predetermined direction and length via the one or more handles, using the measurement markings on the docking piece for reference, to produce a pair of LRIs, each having an accurate depth, length, and arcuate path.

The present invention accommodates creating efficient, accurate, and reproducible LRIs without requiring use of a laser.

BRIEF DESCRIPTION OF THE DRAWINGS

The drawings constitute a part of this specification and include exemplary embodiments of the present invention illustrating various objects and features thereof.

FIG. 1 is a vertical, cross-sectional view of an ophthalmic incisional (e.g., LRI) instrument comprising an embodiment or aspect of the present invention, shown placed on an LRI treatment patient's eye.

DETAILED DESCRIPTION OF THE PREFERRED EMBODIMENTS

I. Introduction and Environment

Figure 3:
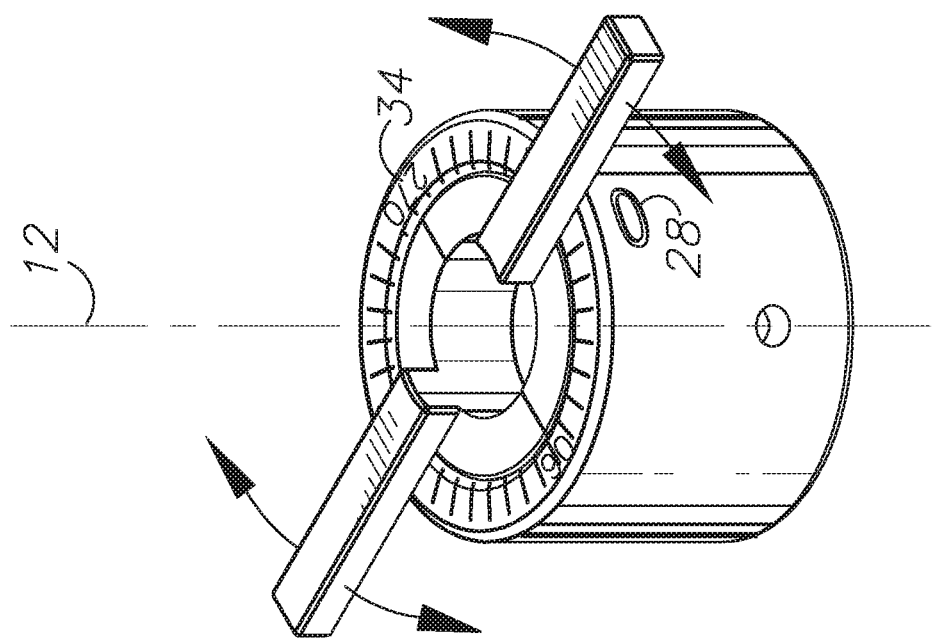
FIG. 3 is an upper, perspective, assembled view of the incisional instrument.

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right, and left refer to the invention as orientated in the view being referred to. The words "inwardly" and "outwardly" refer to directions toward and away from, respectively, the geometric center of the aspect being described and designated parts thereof. Additionally, anatomical terms are given their usual meanings. For example, proximal means closer to the trunk of the body, and distal means further from the trunk of the body. Said terminology will include the words specifically mentioned, derivatives thereof, and words of similar meaning.

II. Preferred Embodiment Ophthalmic Incisional Instrument 2

In a preferred embodiment of the present invention, shown in FIGS. 1-8, an incisional instrument 2 is configured for use in cutting accurate and reproducible limbal relaxing incisions (LRIs) for correcting corneal astigmatism. However, alternative embodiments of the present invention can be used for making any other type of arcuate, surgical incisions or any other non-surgical, arcuate cuts. In a preferred embodiment, the incisional instrument 2 includes two coaxial pieces: a docking piece 4 and a cutting piece 6. The pieces 4, 6 are generally coaxial about a rotational axis 12. The cutting piece 6 is configured for being inserted into the docking piece 4 and is rotatable therein.

In this embodiment, each piece is generally cylindrical in shape, with an open center. The docking piece 4 is configured for being secured to a patient's eye with suction. The cutting piece 6, in this embodiment, is configured for mounting a pair of cutting blades 8 and for fitting coaxially within the docking piece 4 when the instrument 2 is assembled. The cutting piece 6 cutting blades 8 are each of a precise length so that when the cutting piece 6 is flush up against and within the docking piece 4, each cutting blade 8 extends beyond the bottom, or proximal side, of the docking piece 4 a length equal to a desired depth of incisions to be cut. The cutting piece 6 also includes one or more handles 10 for rotating the cutting piece 6 relative to the docking piece 4 to make arcuate incisions.

The docking piece 4 has a cylindrical surface 22 and includes a suction chamber 14 open to the proximal side, or bottom, for accommodating firm, releasable attachment to the sclera, just outside the corneal limbus, of a patient's eye 42 by suction. The docking piece 4 is made of a rigid material which holds its shape under force or pressure. In a preferred embodiment, the docking piece 4 is made of hard plastic, but other embodiments may be made of other rigid materials such as, but not limited to, metal or ceramic. The outer edge surface of the docking piece 4, in this embodiment, includes a side opening 16 to the suction chamber 14 through which sub-atmospheric or negative pressure, or suction, can be applied to the suction chamber 14. In a preferred embodiment, the side opening 16 is sized to fit and seal around tubing connected to a syringe 18 for applying sub-atmospheric pressure, or negative pressure, to the suction chamber 14, as shown in FIG. 1. However, alternative embodiments may include tubing connected to a vacuum or sub-atmospheric pressure source configured for applying sub-atmospheric pressure to the suction chamber 14 through the side opening 16 or any other mechanism for applying sub-atmospheric pressure to the suction chamber 14 through the opening 16.

The docking piece 4 further includes an open center 24 configured for the cutting piece 6 to fit inside and for a surgeon to see through the docking piece 4 below to a patient's eye 42. The docking piece open center 24 forms a receiver for the cutting piece 6. The docking piece open center 24 includes a larger center opening at its distal end and a step portion 26 for providing a mechanical stop for the cutting piece 6 when the cutting piece is inserted into the docking piece 4. The larger opening above the step portion 26 is sized to fit flush around the cylindrical outer surface 30 of the cutting piece 6, with the step 26 contacting the proximal side, or underside, of the cylindrical surface 30 of the cutting piece 6 when the incisional instrument 2 is fully assembled. The portion of the central opening 24 of the docking piece 4 proximally from, or beneath, the step portion 26 is sized to fit flush around the cutting blades 8 of the cutting piece 6.

The cutting piece 6, in the exemplary embodiment shown in FIGS. 1-8, includes a cylindrical outer surface 30 mounting two cutting blades 8 and having an open center 32. The cutting blades 8 are configured for being equal in length and are positioned in 180-degree opposed relation, mounted from the proximal end of the cylindrical outer surface 30 of the cutting piece 6. In this arrangement, the cutting blades 8 are configured for making two symmetrical cuts of equal length, depth, and curvature. In alternative embodiments, the cutting piece 6 may only mount one cutting blade 8 configured for making one arcuate cut at a time. In further alternative embodiments, the cutting piece 6 may include more than two cutting blades 8 spaced apart as necessary for desired cutting configurations. The cutting piece 6 also includes one or more handles 10 for rotating the cutting piece 6 relative to the docking piece 4. In the embodiment shown in FIGS. 1-8, the cutting piece 6 includes two handles 10, which provide torque for effective rotation of the cutting piece 6 in either direction. Alternative embodiments may include only one handle 10 or any number of handles 10, as desired, for rotating the cutting piece 6 relative to the docking piece 4. Further embodiments may include a cutting piece 6 without a center opening 32.

The mechanical stop for the cutting piece 6 in assembled position within the docking piece 4 provided by the step portion 26 of the docking piece 4 is configured for keeping the cutting blades 8 exposed beyond the proximal end, or bottom, of the docking piece 4 a length equal to the desired incision depth. In an exemplary embodiment, the cutting blades 8 are made up of metal capable of making accurate surgical incisions. In alternative exemplary embodiments, the cutting blades 8 may be diamond-shaped for making surgical incisions or any other configurations of suitable materials capable of making accurate incisions. Different lengths of cutting blades 8 may be used as desired for making incisions having different desired depths.

In an exemplary embodiment, the cutting blades 8 are detachable from the cutting piece 6 and replaceable with cutting blades 8 of another length. In such embodiments, the cutting blades 8 may connect into an inner surface of the cutting piece cylindrical surface 30. In other embodiments, cutting blades 8 are permanently affixed to the cutting piece 6. In such embodiments, different cutting pieces 6 having different sizes of cutting blades 8 would be available to surgeons depending on the desired depth of incisions to be made. Similarly, in preferred embodiments, different sizes of docking pieces 4 having varying diameters and corresponding cutting pieces 6 with corresponding varying diameters are available to surgeons depending on the dimensions of the patient's eye to be treated. In various embodiments, the cutting blades 8 may be disposable or configured for reuse after proper sterilization. Additionally, in some embodiments, the entire incisional instrument 2 may be disposable or configured for reuse after proper sterilization. Other embodiments may include a reusable docking piece 4 with a disposable cutting piece 6 or any other combination of disposable and reusable individual pieces.

The incisional instrument 2 of the present invention further includes measurement markings 36 and one or more reference markings 38 for measuring the arcuate incisions made with the instrument 2. In a preferred embodiment, the docking piece 4 includes measurement markings 36 on the distal side, or top, of the docking piece cylindrical surface 22. In the exemplary embodiment shown in FIGS. 1-8, the measurement markings 36 represent degrees, from 0 to 360 degrees, with representative rotational indicia 34 providing references for the surgeon. However, in alternative embodiments, the measurement markings 36 may represent radians, gradians, revolutions, or any other units of measurement of an angle. Optionally, the docking piece 4 may further include one or more rotational indicia measurement markings 28 on the outer edge of the docking piece cylindrical surface 22 for the surgeon to reference, as shown by the "0" marking on the outer edge of the docking piece cylindrical surface 22 in FIGS. 2 and 3.

The incisional instrument 2 further includes one or more reference markings 38 on the cutting piece 6 for aligning the cutting piece 6 with the measurement markings 36 on the docking piece 4. The measurement markings 36 and reference markings 38 allow the user to effectively make cuts with the cutting blades 8 in the correct, desired incision locations. Preferably, the cutting piece reference markings 38 are located on the distal side, or top, of the cutting piece cylindrical surface 30 directly above, or distally from, the cutting blades 8. However, in alternative embodiments, the cutting piece reference markings 38 may be offset from the cutting blades 8, for instance, 90 degrees from the cutting blades 8. In the preferred embodiment shown in FIGS. 1-8, the handles 10 of the cutting piece 6 are offset from the cutting blades 8 and reference markings 38 by 90 degrees, accommodating easy alignment of the reference markings with the measurement markings 36 on the docking piece 4. Alternatively, the handles 10 may be directly above, or distal from, the cutting blades 8 or in any other handle configuration.

Prior to using the incisional instrument 2 of the present invention to perform symmetrical and precise limbal relaxing incisions (LRIs), a surgeon would first mark the patient's eye 42 with a marking pen at the desired locations for the starting point of incisions in the surgical limbus. Next, the docking piece 4 of the incisional instrument 2 is placed on the patient's eye 42 just outside and adjacent to the surgical limbus and the desired incision locations. With the docking piece 4 in proper position on the eye 42, sub-atmospheric pressure is applied to the suction chamber 14 of the docking piece 4 through the side opening 16 via a syringe 18 or some other sub-atmospheric or negative pressure mechanism. Sub-atmospheric pressure applied to the suction chamber 14 attaches the docking piece 4 to the eye 42 and docks the docking piece 4 in the proper position. Next, using the measurement markings 36 and reference markings 38, the cutting piece 6, with cutting blades 8 of a desired length to achieve incisions of the desired depth, is properly aligned with the docking piece 4 so that the cutting blades 8 are aligned with the desired incision starting points. Once properly aligned, the cutting piece 6 is inserted into the docking piece center opening 24, with the step portion 26 providing a mechanical stop for the cutting piece 6 and resulting in the cutting blades 8 cutting into the patient's eye 42 a desired incisional depth. Once assembled, with the cutting blades 8 cutting into the patient's eye 42, the cutting piece 6 is rotated with the handles 10 relative to the docking piece 4 and the eye 42 for a desired incisional length, using the measurement markings 36 and reference markings 38 to measure the incisions. This process guides the cutting blades 8, resulting in two symmetrical, arcuate incisions of equal depth, length, and curvature. Most commonly, a surgeon would hold the docking piece 4 with his or her non-dominant hand while rotating the cutting piece 6 with his or her dominant hand when performing the LRIs. Once the incisions have been made, the cutting piece 6 is removed from the docking piece 4, sub-atmospheric pressure is removed from the docking piece suction chamber 14 to release the docking piece 4 from the patient's eye 42, and the docking piece 4 is removed from the patient's eye 42.

FIG. 1 shows a cross-sectional, environmental view of an embodiment of the incisional instrument 2 of the present invention with the cutting blades 8 making incisions into the surgical limbus of a patient's eye 42. For reference, FIG. 1 includes some anatomical features of the human eye, including the corneal dome, or cornea; sclera; iris; pupil; lens; suspensory ligament; ciliary body; and a reference to the location of the retina. The surgical limbus, also known as the corneal limbus or simply the limbus, is located at the intersection of the cornea and the sclera and is the desired location for making limbal relaxing incisions (LRIs). In this embodiment, sub-atmospheric pressure is applied to the suction chamber 14 via a syringe 18 through the side opening 16 to the suction chamber 14. Sub-atmospheric pressure in the suction chamber 14 provides attachment of the docking piece 4 to the sclera of the patient's eye 42, docking the docking piece 4 just outside of and adjacent to the corneal limbus. The cutting piece 6 fits flush within the open center 24 of the docking piece cylindrical surface 22. The step portion 26 of the docking piece 4 provides a mechanical stop to the cylindrical surface 30 of the cutting piece 6. With the proximal side of the cutting piece cylindrical surface 30 flush against the step portion 26 of the docking piece 4, the cutting blades 8, mounted from the cutting piece cylindrical surface 30, are flush against the sides of the narrower portion of the docking piece open center 24 proximally from the step portion 26. The cutting blades 8 further extend proximally beyond the proximal end of the docking piece 4 and into the patient's eye 42 at the surgical limbus a desired length, forming incisions of a desired depth. FIG. 1 further shows a handle 10 of the cutting piece 6, which the surgeon can use to rotate the cutting piece 6 relative to the docking piece 4 and the patient's eye 42 as necessary to make the desired LRIs.

Figure 2:
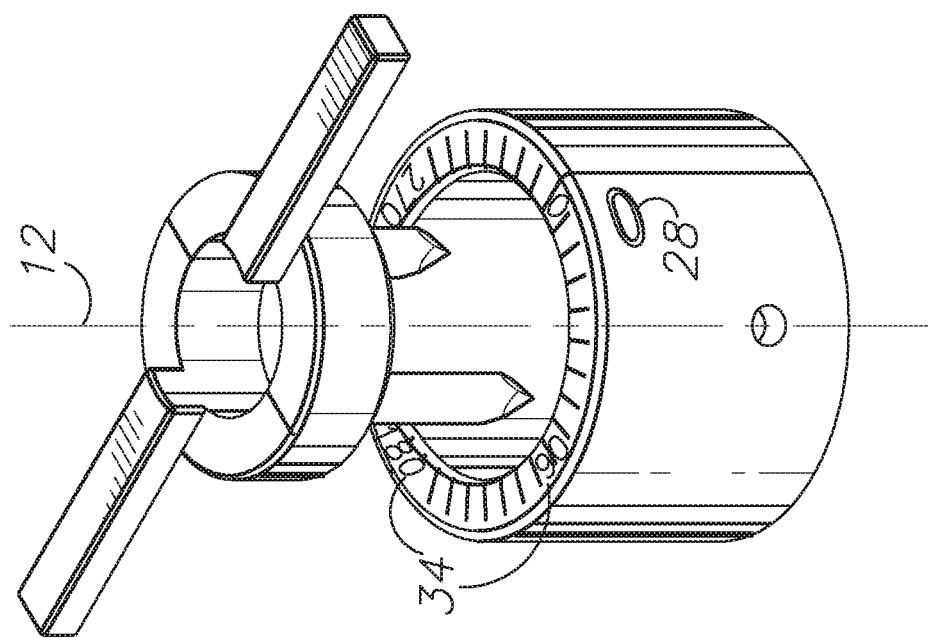
FIG. 2 is an upper, perspective, exploded view of the incisional instrument.

FIG. 2 shows an exploded view of the incisional instrument 2, with the cutting piece 6 separate from and above the docking piece 4. FIG. 2 illustrates the docking piece 4 having an open center 24 and the cutting piece 6 also having an open center 32. The cylindrical surface 30 of the cutting piece 6 is sized to fit within the docking piece open center 24. Further, FIG. 2 particularly illustrates the measurement markings 36 and representative rotational indicia 34 on the distal side of the docking piece 4 and the reference markings 38 on the distal side of the cutting piece 6 for alignment with the measurement markings 36 of the docking piece 4. This embodiment also includes rotational indicia 28 on the side of the docking piece cylindrical surface 22 for reference for the surgeon. In this embodiment, the measurement markings 36 represent degrees. However, as mentioned above, alternative units of angular measurement can be used instead. FIG. 2 shows a preferred embodiment having the reference markings 38 placed above the cutting blades 8 on the distal side of the cutting piece 6 for identification of the location of the cutting blades 8. In this embodiment, the handles 10 are offset 90 degrees from the cutting blades 8 and the reference markings 38 for easy alignment with the measurement markings 36 of the docking piece 4. FIG. 2 also shows the side opening 16 through the outer surface of the docking piece cylindrical surface 22 to the suction chamber 14.

FIG. 3 is an assembled view of the incisional instrument 2 of the present invention, with the cutting piece 6 fully inserted into the center of the docking piece 4, the pieces 4, 6 sharing a rotational axis 12. The cutting piece open center 32 allows a surgeon using the incisional instrument 2 to see through to an underlying patient's eye 42 below with the incisional instrument 2 in assembled position. FIG. 3 shows the alignment of the reference markings 38 with the measurement markings 36 in assembled position for properly positioning and measuring incisions being made with the incisional instrument 2. Directional arrows 46 illustrate that the handles 10 can be used to rotate the cutting piece 6 in either rotational direction relative to the docking piece 4, as desired.

Figure 5:
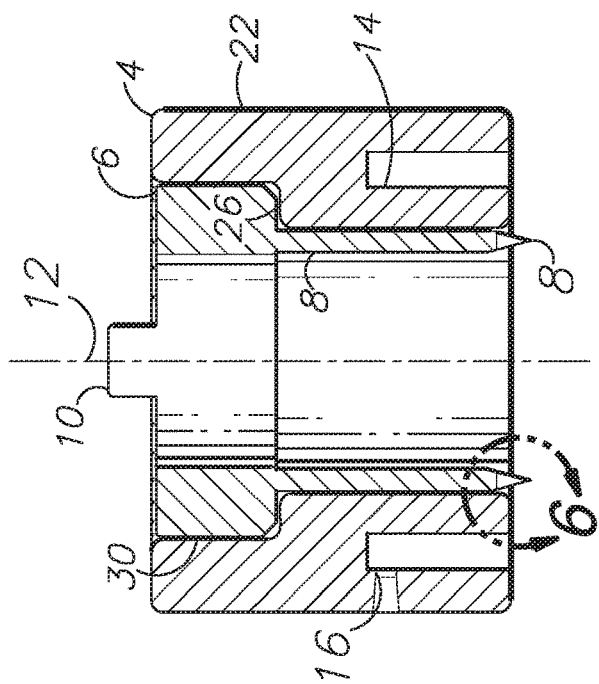
FIG. 5 is a vertical, cross-sectional view of the incisional instrument.
Figure 4:
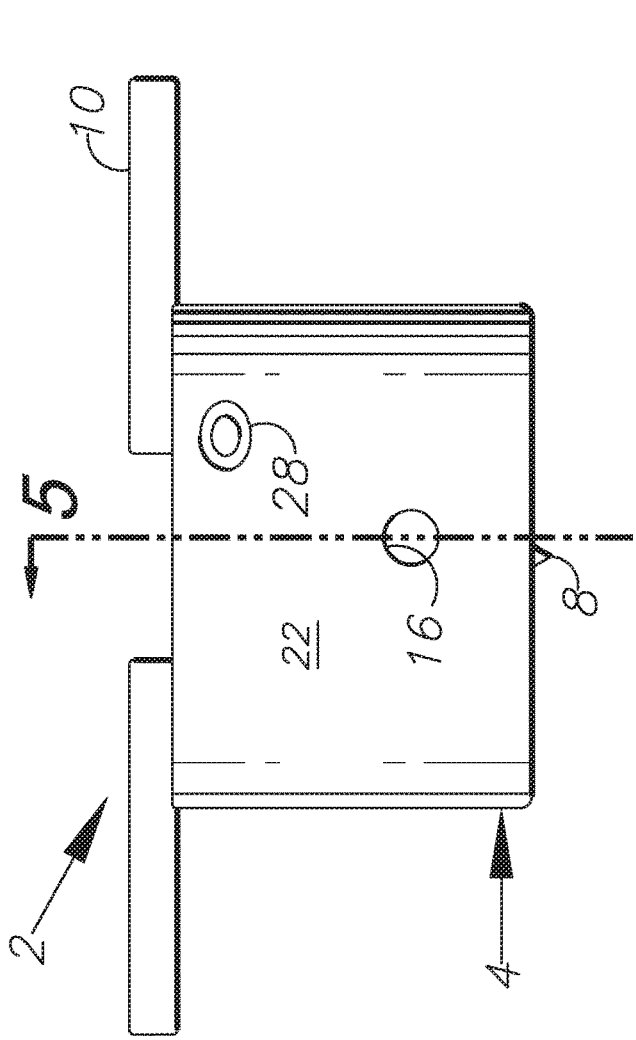
FIG. 4 is a side, elevational view of the assembled incisional instrument.
Figure 6:
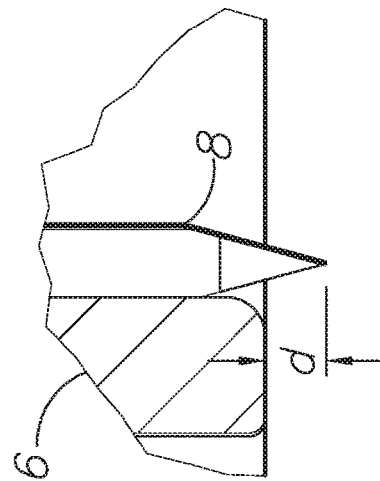
FIG. 6 is an enlarged, fragmentary, cross-sectional view of the incisional instrument showing a cutting blade extending beyond the proximal end of the docking piece in an assembled configuration, taken generally within circle 6 in FIG. 5.

FIG. 4 is a side, elevational view of the incisional instrument 2. Primarily, FIG. 4 displays a cutting blade 8 extending beyond the proximal end of the cylindrical surface 22 of the docking piece 4. FIG. 5 shows a vertical, cross-sectional view of the incisional instrument 2. This cross-section, as shown generally by line 5 in FIG. 4, cuts through the side opening 16 from the outer edge of the docking piece cylindrical surface 22 to the suction chamber 14. The cross-section in FIG. 5 shows the step portion 26 of the docking piece 4 providing a stop for the cylindrical surface 30 of the cutting piece 6 in assembled position. In assembled position, the cutting blades 8, which are mounted from the cutting piece cylindrical surface 30 in an arrangement narrower than the portion of the docking piece center opening 24 proximal from the step portion 26, extend proximally from the cutting piece cylindrical surface 30 and beyond the proximal end of the docking piece 4. FIG. 6 shows an enlarged, fragmentary, vertical, cross-sectional view, taken generally from within circle 6 in FIG. 5, of a cutting blade 8 of the incisional instrument 2 extending proximally past the proximal end of the docking piece 4 by a dimension d. Dimension d is equal to the desired depth of incision.

Figure 8:
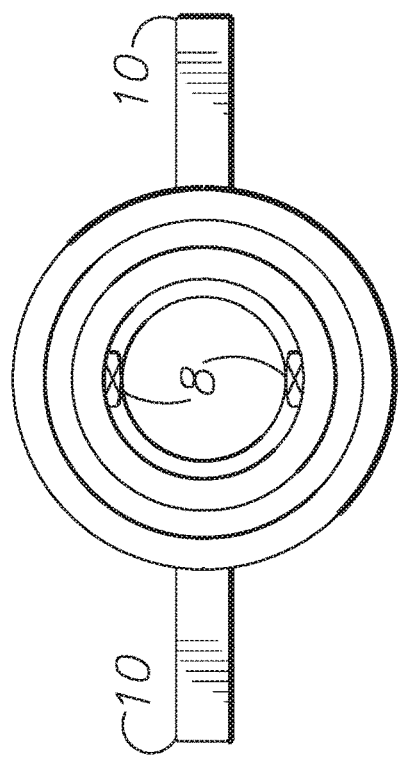
FIG. 8 is a bottom, plan view of the incisional instrument.
Figure 7:
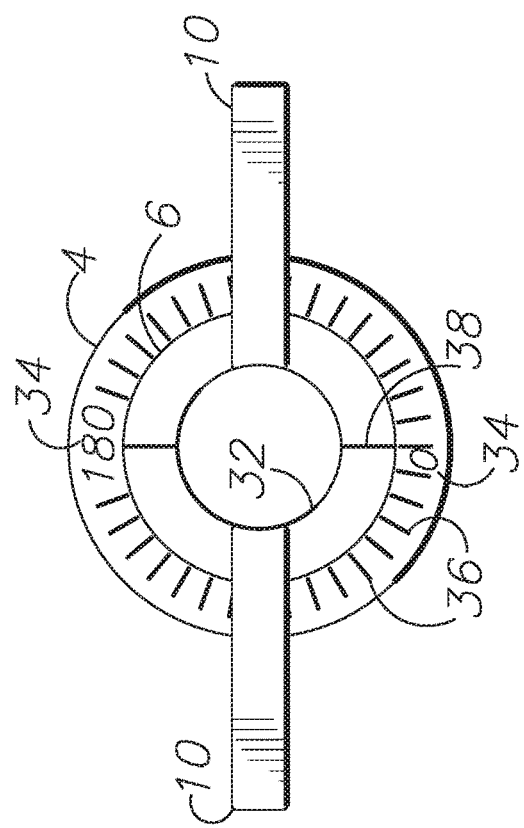
FIG. 7 is a top, plan view of the incisional instrument.

FIG. 7 shows a top, plan view of the incisional instrument 2. FIG. 7 illustrates the open center 32 of the cutting piece 6, the measurement markings 36 on the docking piece 4, and the reference markings 38 on the cutting piece 6, with the handles 10 offset by 90 degrees from the reference markings 38. FIG. 7 further illustrates reference rotational indicia 34. In this embodiment, the measurement markings 36 and rotational indicia 34 represent degrees from 0 to 360 degrees. FIG. 8 is a bottom, plan view of the incisional instrument 2. FIG. 8 shows the open center 32 of the cutting piece 6. FIG. 8 further shows the open proximal end of the suction chamber 14 of the docking piece 4, which is configured for attachment to a patient's eye 42. The cutting blades 8 are mounted from the cutting piece 6. In this embodiment, the handles 10 are radially spaced from the locations of the cutting blades 8 by approximately 90 degrees relative to the axis 12 by 90°, although other cutting blade and handle configurations, spacings and multiples are within the scope present invention.

It is to be understood that the invention can be embodied in various forms and is not to be limited to the examples specifically discussed above. The range of components and configurations which can be utilized in the practice of the present invention is virtually unlimited.

The invention claimed is:

1. An ophthalmic incisional instrument for making a limbal relaxing incision (LRI) on a patient's eye having a sclera, a cornea, and a corneal limbus, the instrument comprising:

a docking piece having proximal and distal ends and a receiver extending between said docking piece ends;

said docking piece proximal end configured for placement on the sclera of said patient's eye;

said docking piece comprising an open center accommodating alignment of said docking piece on said sclera of said patient's eye;

a cutting piece having proximal and distal ends and a rotational axis extending between said cutting piece ends;

said cutting piece configured for insertion into said docking piece receiver and for rotation relative to said docking piece about said rotational axis in an assembled configuration of the instrument;

said cutting piece including a cutting blade extending proximally from said docking piece proximal end a fixed extension length approximately equal to a desired LRI incisional depth, with said instrument in said assembled configuration;

said docking piece further comprising a suction chamber open at said docking piece proximal end;

said docking piece is configured for releasable attachment to the sclera of said patient's eye via sub-atmospheric pressure in said suction chamber;

said docking piece receiver comprises a larger opening portion at said docking piece distal end and a smaller opening portion proximally from said larger opening portion forming a step portion;

said cutting piece including a substantially cylindrical surface;

said step portion providing a mechanical stop for said cutting piece cylindrical surface in said assembled configuration preventing further extension of said cutting blade into said patient's eye beyond said fixed extension length;

said cutting blade configured for forming an arcuate LRI in said patient's eye coaxial to said rotational axis; and wherein said docking piece distal end further comprises measurement markings configured for accommodating measurement of incisions.

2. The incisional instrument according to claim 1, wherein:

said docking piece further comprises a side opening to said suction chamber; and said suction chamber side opening is configured for sealable attachment to a sub-atmospheric pressure source.

3. The incisional instrument according to claim 2, wherein:

said sub-atmospheric pressure source comprises a syringe.

4. The incisional instrument according to claim 2, wherein:

said sub-atmospheric pressure source comprises a vacuum; and said sealable attachment comprises tubing configured for connecting said vacuum to said suction chamber via a sealed connection through said side opening.

5. The incisional instrument according to claim 1, wherein:

said cutting piece includes two cutting blades.

6. The incisional instrument according to claim 5, wherein:

said cutting blades are positioned in 180-degree opposed relation; and said cutting blades are configured for making symmetrical incisions of equal length, depth, and curvature.

7. The incisional instrument according to claim 1, wherein:

said cutting piece further comprises a handle on said cutting piece distal end; and said handle accommodates efficient rotation of said cutting piece relative to said docking piece.

8. The incisional instrument according to claim 1, wherein:

said measurements markings are located on the distal side of said docking piece; and said cutting piece further comprises a reference marking for aligning with said docking piece measurement markings;.

9. The incisional instrument according to claim 1, wherein:

said measurement markings are selected from the group consisting of: degrees, radians, gradians, and revolutions.

10. The incisional instrument according to claim 1, wherein:

said cutting blade is detachable; and said cutting blade is configured for detachment and for replacement with a cutting blade of a desired alternative length.

11. An ophthalmic incisional instrument for making limbal relaxing incisions (LRIs) on a patient's eye having a sclera, a cornea, and a corneal limbus, the instrument comprising:

a docking piece having proximal and distal ends and a receiver extending between said docking piece ends;

said docking piece proximal end configured for placement on the sclera of said patient's eye;

said docking piece comprising an open center accommodating alignment of said docking piece on said sclera of said patient's eye;

said docking piece including a suction chamber open at said docking piece proximal end;

said docking piece including a side opening to said suction chamber;

said suction chamber side opening configured for sealable attachment to a sub-atmospheric pressure source;

said docking piece configured for releasable attachment to the sclera of said patient's eye via sub-atmospheric pressure in said suction chamber;

a cutting piece including a substantially cylindrical surface having proximal and distal ends and a rotational axis extending between said cutting piece cylindrical surface ends;

said cutting piece configured for insertion into said docking piece receiver and for rotation relative to said docking piece about said rotational axis in an assembled configuration of the instrument;

said docking piece receiver comprising a larger opening portion at said docking piece distal end and a smaller opening portion proximally from said larger opening portion forming a step portion;

said cutting piece mounting two cutting blades extending proximally from said cutting piece cylindrical surface proximal end and positioned in 180-degree opposed relation;

said cutting blades extending proximally from said docking piece proximal end a fixed extension length equal to a desired LRI incisional depth, with said instrument in said assembled configuration;

said step portion providing a mechanical stop for said cutting piece cylindrical surface in said assembled configuration preventing further extension of said cutting blades into said patient's eye beyond said fixed extension length;

said cutting blades configured for forming a pair of symmetrical, arcuate LRIs in said patient's eye coaxial to said rotational axis;

said cutting piece including a handle on said distal end of said cutting piece cylindrical surface;

said handle configured for accommodating efficient rotation of said cutting piece relative to said docking piece about said rotational axis;

said docking piece including measurement markings on the distal side of said docking piece;

said cutting piece including a reference marking for aligning with said docking piece measurement markings;

said measurement markings and said reference marking configured for accommodating measurement of incisions; and said measurement markings are selected from the group consisting of: degrees, radians, gradians, and revolutions.

12. An ophthalmic method for making a limbal relaxing incision (LRI) on a patient's eye having a sclera, a cornea, and a corneal limbus with an incisional instrument including a docking piece having proximal and distal ends, an open center accommodating alignment, a suction chamber open at the docking piece proximal end, and a receiver extending between the docking piece ends; the docking piece receiver including a larger opening portion at the docking piece distal end and a smaller opening portion proximally from said larger opening portion forming a step portion; a cutting piece having proximal and distal ends and a rotational axis extending between the cutting piece ends; the cutting piece including a substantially cylindrical surface and configured for insertion into the docking piece receiver and for rotation relative to the docking piece about the rotational axis in an assembled configuration of the instrument; the cutting piece including a cutting blade extending proximally from the docking piece proximal end a fixed extension length approximately equal to a desired LRI incisional depth with the instrument in the assembled configuration; and wherein said docking piece distal end further comprises measurement markings configured for accommodating measurement of incisions; the method comprising the steps of:

aligning said docking piece proximal end on the sclera of said patient's eye, utilizing said docking piece open center;

applying sub-atmospheric pressure to said suction chamber, attaching said docking piece to said sclera of said patient's eye;

aligning said cutting piece with said docking piece and said patient's eye as desired;

placing said cutting piece within said docking piece receiver in said assembled position, inserting said cutting blade into said patient's eye at the desired LRI location;

said step portion stopping said cutting piece cylindrical surface and preventing further extension of said cutting blade into said patient's eye beyond said fixed extension length;

rotating said cutting piece relative to said docking piece about said rotational axis a desired direction and length, forming an arcuate LRI in said patient's eye coaxial to said rotational axis; and removing said cutting piece and said docking piece from said patient's eye.

13. The method according to claim 12, further comprising the step of:

removing sub-atmospheric pressure from said docking piece suction chamber.

14. The method according to claim 12, wherein:

said cutting piece includes two cutting blades positioned in 180-degree opposed relation; and said cutting blades are configured for making symmetrical incisions of equal length, depth, and curvature.

15. The method according to claim 12, wherein:

said measurements markings are located on the distal side of said docking piece; and said cutting piece further comprises a reference marking for aligning with said docking piece measurement markings;.

16. The method according to claim 12, further comprising the steps of:

marking a desired LRI location on said patient's eye; and matching up said cutting blade with said marked desired LRI location when placing said cutting piece within said docking piece.

17. The method according to claim 12, wherein said cutting blade is detachable, the method further comprising the steps of:

detaching said cutting blade; and replacing said detached cutting blade with a cutting blade of a desired alternative length.

* * * * *